United States Patent [19]
Davies

[11] 3,989,041
[45] Nov. 2, 1976

[54] MOTION LIMITING SUPPORTIVE DEVICE
[75] Inventor: Richard B. Davies, Parma Heights, Ohio
[73] Assignee: The Kendall Company, Boston, Mass.
[22] Filed: Apr. 14, 1975
[21] Appl. No.: 567,940

[52] U.S. Cl. ............................................. 128/166
[51] Int. Cl.² ...................................... A61F 13/06
[58] Field of Search ................ 128/165, 166, 166.5, 128/157, 80 E

[56] References Cited
UNITED STATES PATENTS

| | | | |
|---|---|---|---|
| 2,484,130 | 10/1949 | Thibault | 128/166.5 |
| 2,658,510 | 11/1953 | Hilton | 128/157 |
| 2,875,758 | 3/1959 | Fuzak et al. | 128/157 |
| 3,508,544 | 4/1970 | Moore et al. | 128/157 |

Primary Examiner—Lawrence W. Trapp
Attorney, Agent, or Firm—Edward J. Scahill, Jr.

[57] ABSTRACT

A single piece of high-tensile elastic adhesive tape which is die-cut in a particular manner so as to form a supportive device that is capable of limiting joint movement. The device comprises a sheet of a conformable, high-tensile, elastic, permanently tacky, pressure-sensitive adhesive tape material that has widthwise stretch but no lengthwise stretch, and is covered, on the adhesive portion thereof, with a sheet of release paper of the same size and shape. The device structure is such as to have a pair of flanging anchor wings on either end of an elongated piece of the adhesive material, and having a pair of angularly set anchor tabs positioned between the pairs of anchor wings. While the device can be stretched across its width at any point thereon, there is no stretch or dead stretch along the length thereof. This attribute serves as a basis for limiting specific joint movement. For example, when it is applied with the intention of limiting ankle inversion, one pair of anchor wings is adhesively secured to the inside of the ankle, just below the ankle bone, while the rest of the device is brought under the foot and up along the outside portion of the ankle and leg. The thusly positioned device is further secured thereto by means of the anchor tabs which encircle the ankle joint, adhesively overlapping the outer edges of the first pair of anchor wings, and the second pair of anchor wings then are adhesively attached to the outer portion of the calf. In this manner, the device limits ankle inversion because it has no stretch along the length thereof, while providing comfort and conformability for the ankle because of the elasticity of the device across its width. Furthermore, because of the predetermined die-cut structure of the device, it permits those persons not specially trained in the traditional techniques of supportive joint strapping to effectively apply and use same. The device also saves labor and time for the skilled athletic trainer when used alone or in conjunction with traditional strapping techniques.

8 Claims, 6 Drawing Figures

MOTION LIMITING SUPPORTIVE DEVICE

BACKGROUND OF THE INVENTION

This invention relates to a motion limiting supportive device, and more particularly, to a single die-cut piece of high-tensile, comformable elastic adhesive tape that will effectively limit a particular motion of certain body joint.

For years, athletic teams especially on the professional and collegiate levels, have employed specially trained professional trainers to apply supportive joint strapping on injured athletes, or athletes who have formerly had problems with joint injuries, for example, ankle injuries. This practice was performed as a treatment and as a preventive step that would provide support for weak joints, i.e., ankles, wrists, etc. On the high school level, many schools could not afford to provide the services of such a trainer, so they would have the coach or the team doctor perform such a service. In this case, many of the coaches and doctors had no special training in the techniques of supportive joint strapping. In either event, the procedure was a lengthy one, with long lines of athletes waiting to be "strapped up" prior to their daily practices and workouts, becoming a rather common occurrence.

Many prior art attempts have been made to provide a supportive joint strapping that would be quicker and easier to apply, while still providing effective support at an economical price. Traditionally, adhesive tape has been used for this purpose and it is still the first choice since the alternatives have been lacking in many respects. However, even adhesive tape has many disadvantages; for example, the number of cuts that must be made, the number of overlapping wraps that must be used, and the amount of special training that the person performing the service must possess. U.S. Pat. No. 3,050,053 describes an orthopedic support having a stretchable limb or joint encircling member and a plurality of non-stretchable straps or tapes which project outwardly from the member in a predetermined angular pattern for binding the limb in a specific manner. This particular support is, however, a complicated array of individual straps which could be applied in the wrong manner by a non-professional; it cannot be adopted for use on any other joint without major modifications; the useful life of the support is severly limited by loss of tack and adhesion in the adhesive straps; and such a device is comparatively costly to produce. Further, this support cannot be applied specifically, but rather, its application limits ankle inversion, eversion and plantar flexion.

Another prior art attempt at providing a joint support is described in U.S. Pat. No. 3,073,305, wherein an elastic sleeve which is stretchable in the circumferential direction and which has an upper ankle receiving portion and a lower foot receiving portion separated by a slit through which the heel can project. A plurality of stays and loops are provided on the sleeve for orienting the support and maintaining same by passing the stays through the loops and securing them in position thereon. Once again, this device is cumbersome to work with, and relatively expensive to use, as well as not providing much comfort to the athlete who must then put his or her shoes or sneakers thereover. Also, there is no adhesive provided thereon with which to hold the unit to a limb, therefore, the ankle may slip within the elastic sleeve.

Still another, and earlier, prior art device is shown and described in U.S. Pat. No. 991,831. However, this device was designed primarily for comfort, and did not provide the support needed by athletes competing in modern athletic programs today. Many other attempts have been made to obtain a simple, efficient, economical and compact means for providing a supportive motion limiting device, but, until now, no satisfactory device has been found.

Accordingly, it is an object of this invention to provide an adhesive backed, disposable motion limiting supportive device that has no stretch in its linear direction thereby facilitating the limiting of specific joint motion, while still providing comfort and conformability without constriction as a result of the widthwise stretch characteristic of the device.

It is another object of the present invention to provide a joint supportive wrap that can be effectively applied by persons not specially trained in the traditional techniques of supportive joint strapping, and to be a time saving device to those who are so trained, such as professional athletic trainers.

Still another object of this invention is to provide a motion limiting supportive device that can advantageously be adapted for use on many joints of the human body and can control anatomical joint motion in both the vertical and horizontal planes.

A further object of the instant invention is to provide a single, continuous piece of high-tensile, comfortable elastic adhesive tape that is cut in such a manner as to facilitate the easy and effective application of the device on bodily joints.

SUMMARY OF THE INVENTION

A conformable, high-tensile, elastic, pressure-sensitive adhesive tape is cut as to provide a motion limiting supportive device that can be easily and effectively applied even by persons not specially trained in the techniques of supportive joint strapping, and that will serve as a useful adjunct to the strapping methods of the skilled professional. The device has a generally elongated I shape that has a pair of angularly set anchor tabs positioned between opposing pairs of flanging anchor wings disposed on either end of the elongated I. The device is cut from a sheet of elastic adhesive fabric in a predetermined direction so as to provide substantially no stretch along the length of the I, while providing good stretch and conformability across the width of the flanging anchor wings and anchor tabs. Accordingly, for example, when it is desired to limit ankle inversion, one pair of flanging anchor wings are secured to the inside of the ankle just below the ankle bone while the rest of the device is brought under the foot and up along the outside portion of the ankle and lower leg. The thusly positioned device is further secured thereto by means of the intermediately disposed anchor tabs adhesively overlapping the outer edges of the first pair of anchor wings at the ankle joint, and the second pair of anchor wings then are adhesively attached to the outer portion of the calf. Ankle inversion is thereby limited so as to protect the ankle and reduce the likelihood of injury or re-injury, however, because of the one-way elasticity characteristics of the device, the athlete wearing it has comfort and conformability, as well as support.

BRIEF DESCRIPTIONS OF DRAWINGS

DETAILED DESCRIPTION OF THE PREFERRED EMBODIMENTS

Figure 1:
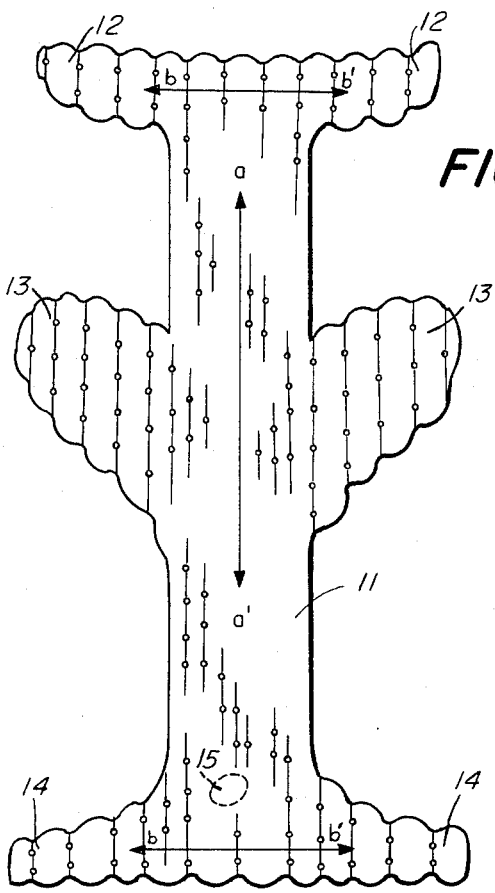
FIG. 1 shows a plan view of the supportive device of this invention further showing the anchor wings and anchor tabs used therein.

A device for limiting joint motion is provided herein whereby a person not previously trained in traditional strapping techniques can effectively apply a means of support to particular injured or weakened joints of the human body. With reference to FIG. 1, there is shown a simple continuous piece of high-tensile elastic tape which is cut in a manner to form a supportive device as previously described above. The device 10 comprises a sheet of conformable, elastic, permanently tacky, pressure-sensitive adhesive tape material 11 that has widthwise stretch along the lines $b$—$b'$ throughout the material 11, while having substantially no stretch along the lengthwise direction as shown by the line $a$—$a'$. The device 10 has a generally I shaped configuration wherein the top and bottom portions of the I are pairs of flanging anchor wings 12 and 14 respectively. A pair of anchor tabs 13 are positioned in an intermediate position between the anchor wings 12 and 14. The tabs 13 are angularly disposed on the device in a manner that points the tabs toward the top of the I configuration and the anchor wings 12.

The elastic adhesive sheet material 11 preferably has a woven, high-tensile strength backing having warp yarns distributed thereon with elastomeric cores. The warp yarns preferably occur in a repeating pattern, but they may be mixed in proper ratio indiscriminately with other non-elastomeric warp yarns. The elastomeric core yarns cause the backing when relaxed to assume a nonplanar character including intermingled raised and depressed areas. The nonelastic warp yarns are preferably of high-tensile strength stretch nylon or the like, while the elastomeric warp yarns are preferably of corespun spandex with a spun portion of rayon or other natural or synthetic yarn, but other spun coverings or yarn wrappings may be used to protect the spandex or other elastomeric cores. Such a tape material and backing can be found in U.S. Pat. No. 3,618,754, of common assignee. As can be seen in FIG. 1, the device assumes a nonplanar character when relaxed including intermingled raised and depressed areas thereon.

Pressure-sensitive adhesives suitable for the device of this invention are not critical. Any of the well known adhesives employed for pressure-sensitive adhesive tapes are suitable and can be used. A sheet of release paper should advantageously cover the adhesive side of the device and may advantageously have tear lines shown at the tab and wing portions thereon which facilitate the application of the device onto the athlete who is in need of support. The sheet material can preferably be die-cut into a taping structure that is approximately 16 inches – 17 inches long and approximately 9 inches – 10 11 inches wide overall, while being approximately 3 inches – 4 inches wide across the narrow portion of the I configuration. For most applications, the portion of the I between the anchor tabs 13 and the anchor wings 14 should be slightly longer than the distance between anchor tabs 13 and anchor wings 12. This structure has been found to be most effective for a majority of taping applications. Furthermore, other modifications can be made in the structure for other applications, for example, a hole 15 can be formed in the midsection of anchor wings 14 for possibly going over and around an injured thumb and can thereby be used to limit the extension thereof.

Figure 2:
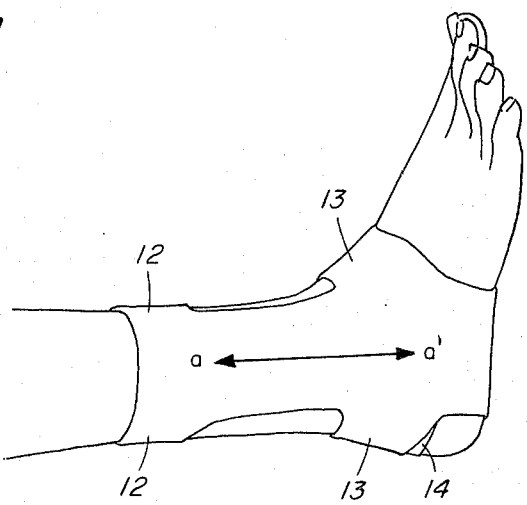
FIG. 2 shows a perspective view of the supportive device of this invention on an ankle and in a position thereon to limit ankle inversion.

The device described above has many applications and can be used, for example, to limit ankle inversion. FIG. 2 shows such an application wherein the anchor wings 14 are placed around the ankle on the inside portion thereof, just below the ankle bone, and the anchor wings 12 are drawn under the foot and secured in place adhesively around the outside of the calf. The anchor tabs 13 further secure the device in place by adhesively overlapping the outer edges of the anchor wings 14 at the ankle joint. Because of the stretch and non-stretch characteristcs of this device, the person wearing the thusly applied tape material, now has a device thereon which will selectively limit ankle inversion while still allowing plantar flexion, comfort and conformability to the wearer. Since there is substantially no stretch along lines $a$—$a'$, ankle inversion is quite effectively limited. Ankle eversion can be limited as well by simply reversing this taping process by starting on the outer portion of the ankle and bringing the device up from under the foot and securing same on the inner portion of the calf. The device has a multitude of uses, for example, immediately following a joint injury such as an ankle sprain to limit specific joint motion that would aggravate the injury and interfere with the healing process; during and after rehabilitation of the injured ankle to reduce the likelihood of re-injury; and, as a preventative adhesive ankle strapping that is worn during competition in order to minimize the incidence of and severity of the common ankle sprain resulting from forced inversion of the ankle.

Figure 3:
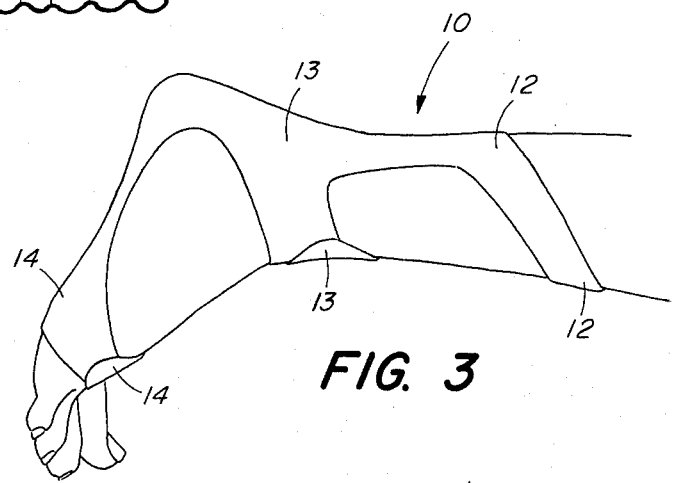
FIG. 3 is another perspective view of the device of this invention located on an ankle in a position thereon that will give support to Achilles tendon by limiting dorsa flexion.

FIG. 3 shows the device 10 being applied in a manner so as to support the Achilles tendon by limiting dorsa flexion. Anchor wings 14 are wrapped over the top of the foot from beneath it while the elongated portion of the device runs up along the bottom of the foot over the heel and on up to the back of the leg and calf wherein anchor tabs 12 are used to set the proper amount of tension desired therein by securing the device to the leg as shown therein. Anchor tabs 13 are then secured at the ankle as a further stabilizing means. Once again, the linear dead-stretch and high-tensile characteristics of this device provide selective support to the Achilles tendon and restrict dorsa flexion, while still allowing plantar flexion and comfort, due to the widthwise stretch capabilities and conformability of the device.

Figure 4:
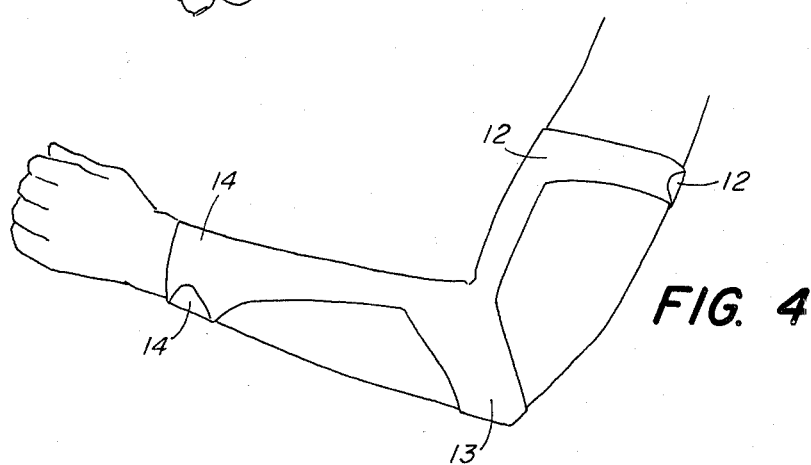
FIG. 4 is a perspective view of this supportive device positioned on an arm and elbow in a manner that will limit elbow extension.

In a like manner elbow extension can be limited by wrapping anchor wings 14 around the wrist, as shown in FIG. 4, positioning the bend of the elbow at the desired position and securing the anchor tabs 13 around the elbow and the anchor wings 12 around the bicep area of the arm.

Figure 5:
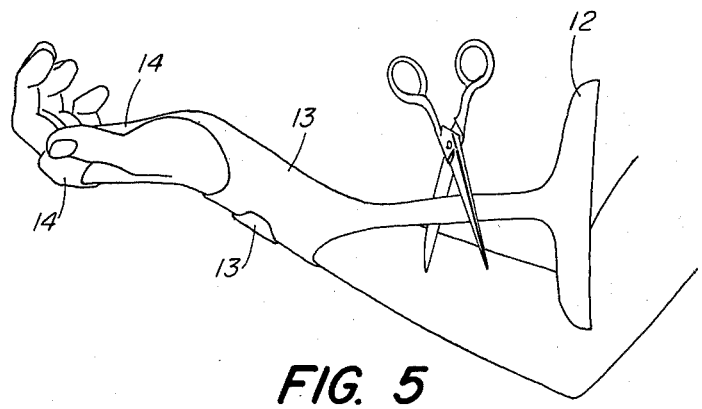
FIG. 5 shows a perspective view of another embodiment of this invention wherein a portion of the device is cut away so as to provide a compact supportive means for limiting wrist extension; and, FIG. 6 shows a perspective view of the device of this invention having release paper thereon.

Wrist extension can be limited as shown in FIG. 5 whereby the anchor tabs 13 are wrapped around the wrist while the anchor wings 14 are secured across the upper portion of the palm of the hand and across the knuckles of the hand. The excess material, including the anchor wings 12, can then be simply cut off or can be folded over on itself to improve the looks of the thusly wrapped wrist.

Figure 6:
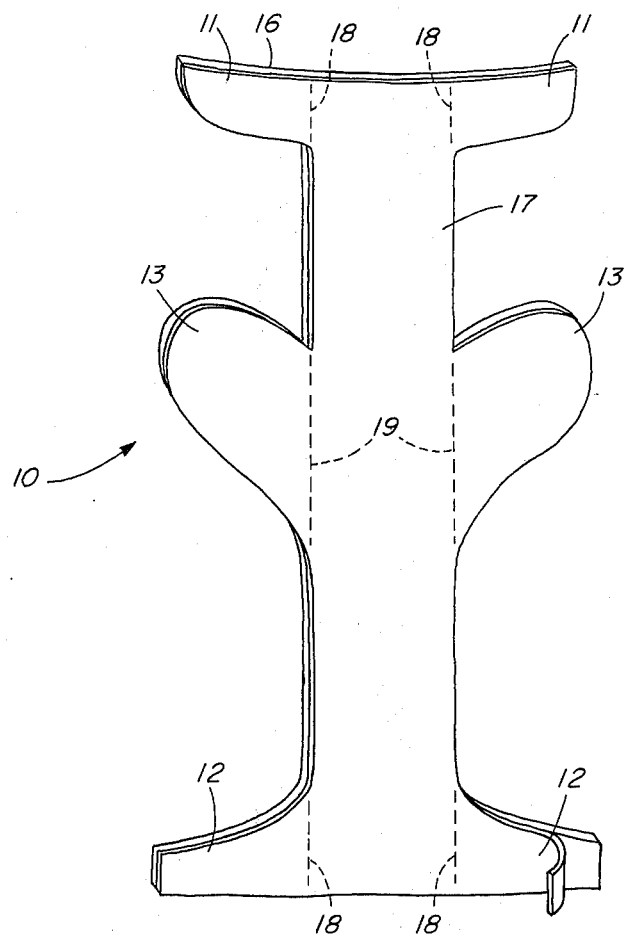

FIG. 6 shows the motion limiting device 10 of this invention having a sheet of release paper 17 over the adhesive 16 on the back of the device 10. The release paper 17 can advantageously be torn by stretching the device in its elastic widthwise direction at the base of each tape, as shown by lines 18 and 19. As the release paper 17 is not elastic, it easily tears when the cloth to which it adheres is stretched. Then, one simply peels the release paper from the middle of the device, leaving the six anchoring portions still covered with release paper. The device can then be handled easily in that only those portions of adhesive material being used at a particular time need be exposed. Of course, as the anchoring portions are applied, the release paper is removed. If the entire sheet of release paper 17 were to be completely removed prior to a subsequent use, the device may tend to become somewhat cumbersome to work with.

Of course, these are but a few of the uses and applications which the motion limiting supportive device of this invention can be used for. The device provides many advantages to traditional strapping techniques wherein the tape is removed from a roll and applied in strips, in that this device can be effectively applied by persons not specially trained in the traditional techniques of supportive joint strapping, for example, nurses, many physicians and many athletic coaches. Furthermore, the anchoring strips that are usually added as separate pieces of a stirrup to hold it in place are a part of this device, thereby providing a direct connection to stabilize the stirrup rather than the simple adhesive bond between the separate stirrup and anchor strips traditionally used. As earlier described herein, the stretch and no-stretch characteristics of this device provide the comfort and comformability traditionally lacking in adhesive strapping techniques. Of course, the wide variety of applications to which this device can be put is a major advantage in and of itself. While the device is effective when used alone, it can be used as a time saving adjunct to traditional strapping techniques by the skilled athletic trainer.

The above-described specific embodiments of this invention have been set forth for the purposes of illustration. It will be apparent to those skilled in the art of supportive devices that various modifications may be made in the ultimate structure of this motion limiting device without departing from the principles of this invention as pointed out and disclosed herein. For that reason, it is not intended that the invention should be limited other than by the scope of the appended claims.

What is claimed is:

1. A motion limiting supportive device comprising: an elastic sheet of conformable, adhesive tape material, said sheet being a generally elongated configuration having oppositely disposed pairs of flanging anchor wings on each end of said elongated configuration and a pair of anchor tabs disposed in an intermediate position along said elongated configuration between said anchor wings, said elastic sheet including high-tensile strength nylon yarns therein and being constructed in a manner that permits widthwise stretch across the device, but provides substantially no lengthwise stretch along said elongated configuration.

2. The motion limiting supportive device of claim 1 wherein said anchor tabs are angularly set and positioned at acute angles at the uppermost portion thereof.

3. The motion limiting supportive device of claim 1 wherein said anchor tabs are positioned closer to the uppermost pair of anchor wings than to said lowermost pair of anchor wings.

4. The motion limiting supportive device of claim 1 wherein said adhesive tape material has a pressure-sensitive adhesive thereon.

5. The motion limiting supportive device of claim 1 wherein said elastic sheet assumes a nonplanar character when relaxed including intermingled raised and depressed areas thereon.

6. The motion limiting supportive device of claim 1 having a release sheet covering said adhesive material.

7. The motion limiting supportive device of claim 6 wherein said release sheet has tear lines across said anchor wing portions and said anchor tab portions.

8. The motion limiting supportive device of claim 1 having a hole formed in the mid-section of one pair of said anchor wings.

* * * * *